(12) United States Patent
Izutsu

(10) Patent No.: US 8,229,065 B2
(45) Date of Patent: Jul. 24, 2012

(54) X-RAY INSPECTION DEVICE

(75) Inventor: Katsunori Izutsu, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 260 days.

(21) Appl. No.: 12/774,922

(22) Filed: May 6, 2010

(65) Prior Publication Data
US 2010/0290589 A1   Nov. 18, 2010

(30) Foreign Application Priority Data

May 13, 2009 (JP) ................................. 2009-116105
Feb. 18, 2010 (JP) ................................. 2010-033442

(51) Int. Cl.
*G01N 23/04* (2006.01)
(52) U.S. Cl. ........................................................ 378/57
(58) Field of Classification Search .................. 378/57, 378/98.8, 145, 147; 250/370.08, 370.09, 250/370.11, 505.1
See application file for complete search history.

(56) References Cited

U.S. PATENT DOCUMENTS

| | | | | |
|---|---|---|---|---|
| 4,366,382 A | * | 12/1982 | Kotowski | 378/57 |
| 6,347,131 B1 | * | 2/2002 | Gusterson | 378/54 |
| 6,512,812 B2 | * | 1/2003 | Watanabe | 378/57 |
| 6,844,570 B2 | | 1/2005 | Sekine et al. | 257/80 |

FOREIGN PATENT DOCUMENTS
JP      2003-84066 A    3/2003
* cited by examiner

*Primary Examiner* — Courtney Thomas
(74) *Attorney, Agent, or Firm* — Global IP Counselors, LLP

(57) ABSTRACT

An X-ray inspection device is adapted to detect foreign matter in a target object while the target object is conveyed. The X-ray inspection device includes an X-ray emission device, a scintillator unit, a slit member and a photodiode array. The scintillator unit extends in a direction that intersects a conveyance direction of the target object, and is configured and arranged to optically convert the X-rays emitted by the X-ray emission device into visible light. The slit member forms a slit that extends in the direction that intersects the conveyance direction, and is disposed on an upstream side of the scintillator unit with respect to a direction of X-ray irradiation. The slit member is arranged so that a width of the slit is narrower than a width of the scintillator unit, and is equal to or wider than half a light-receiving width of the photodiode array in the conveyance direction.

6 Claims, 14 Drawing Sheets

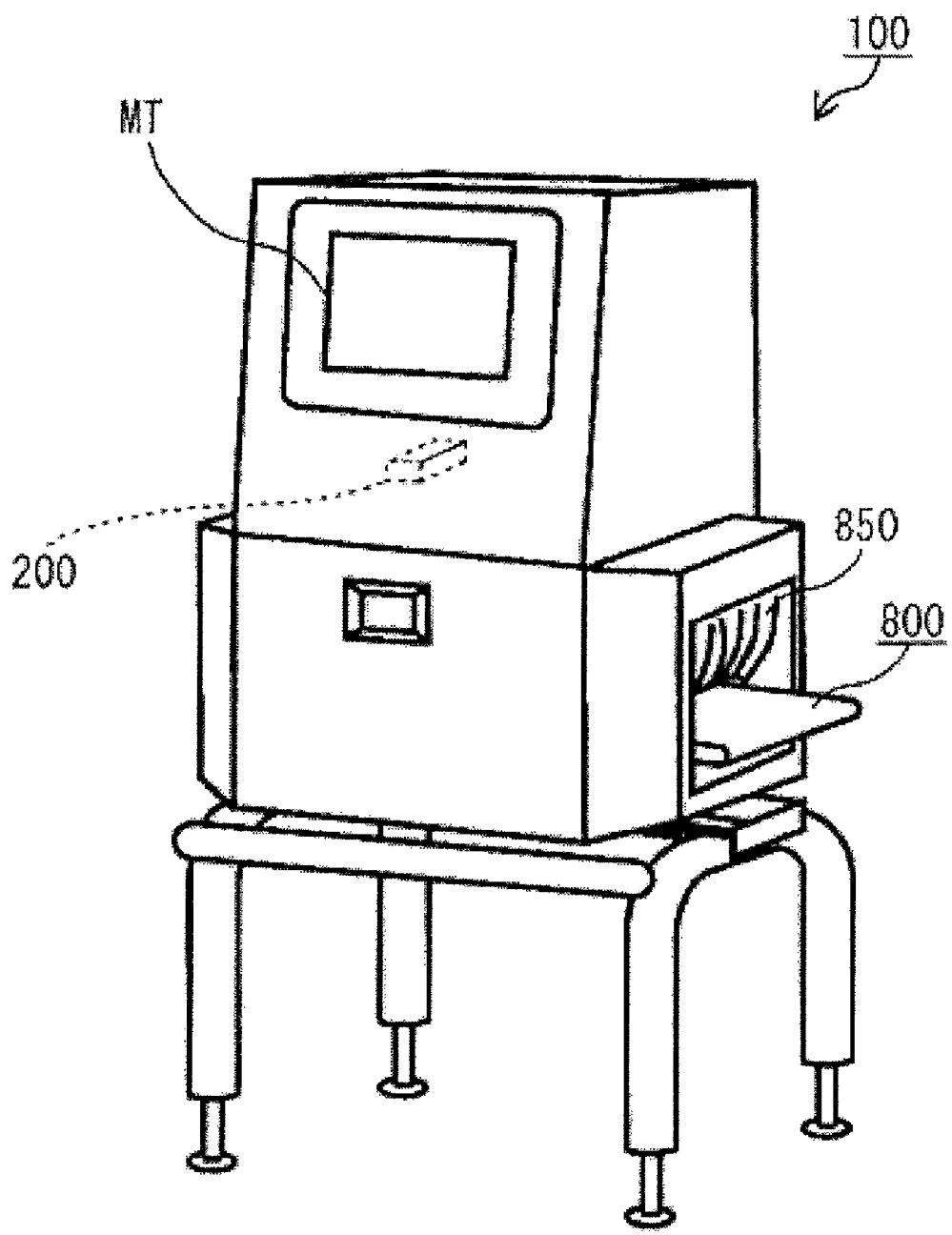
F I G. 1

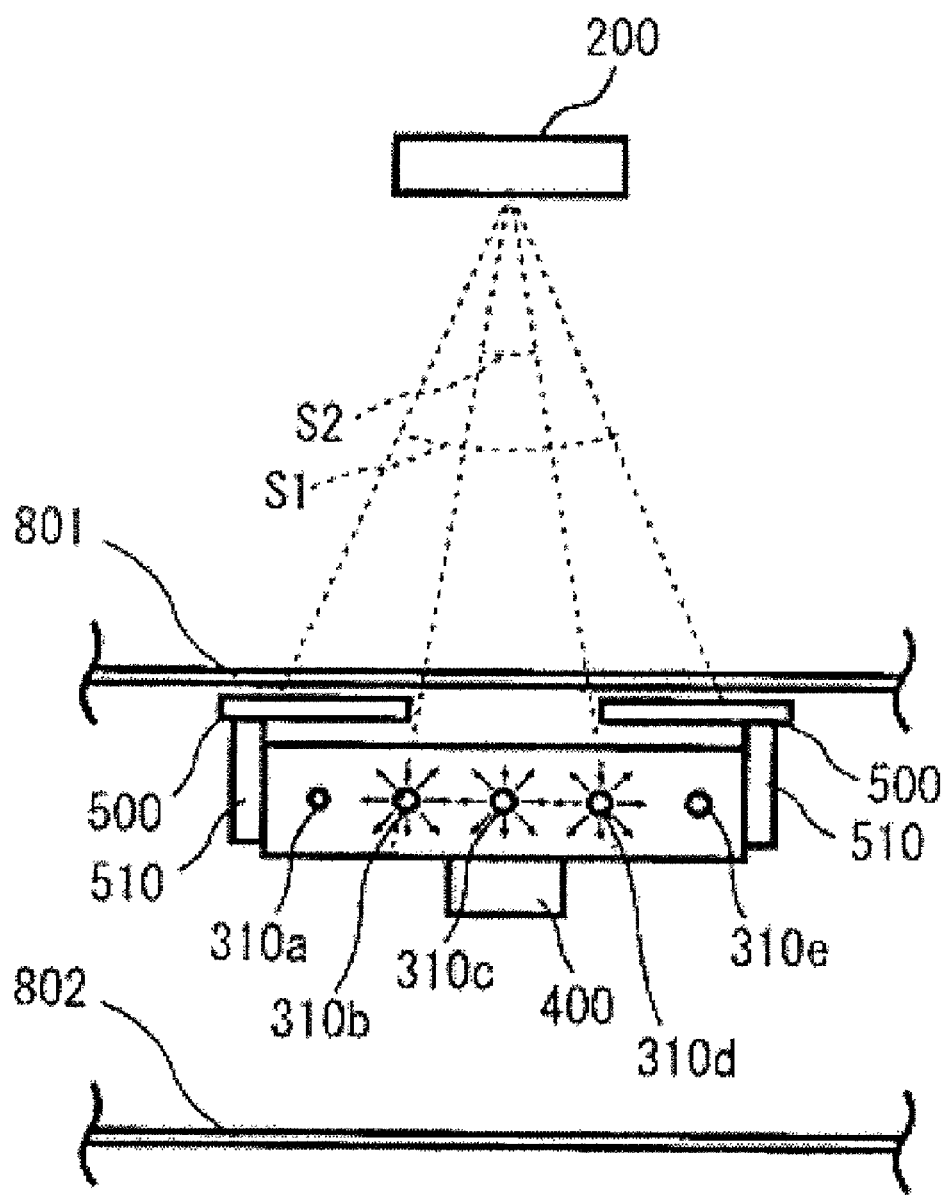
F I G. 3

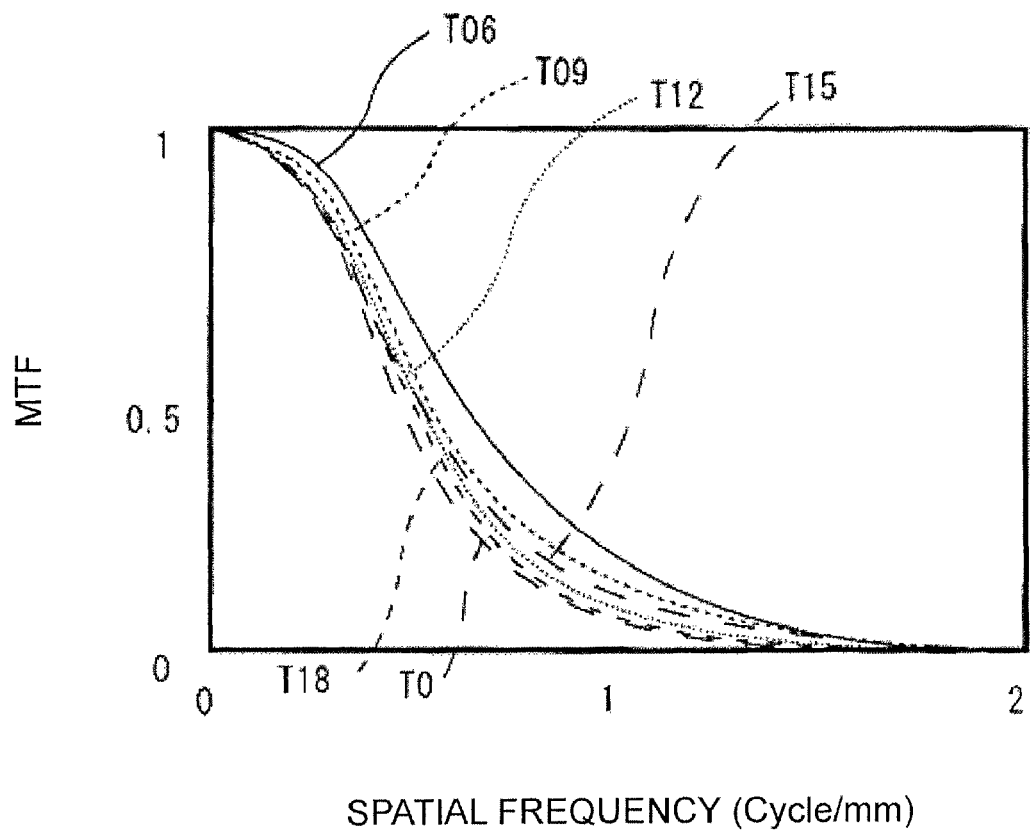
F I G. 6

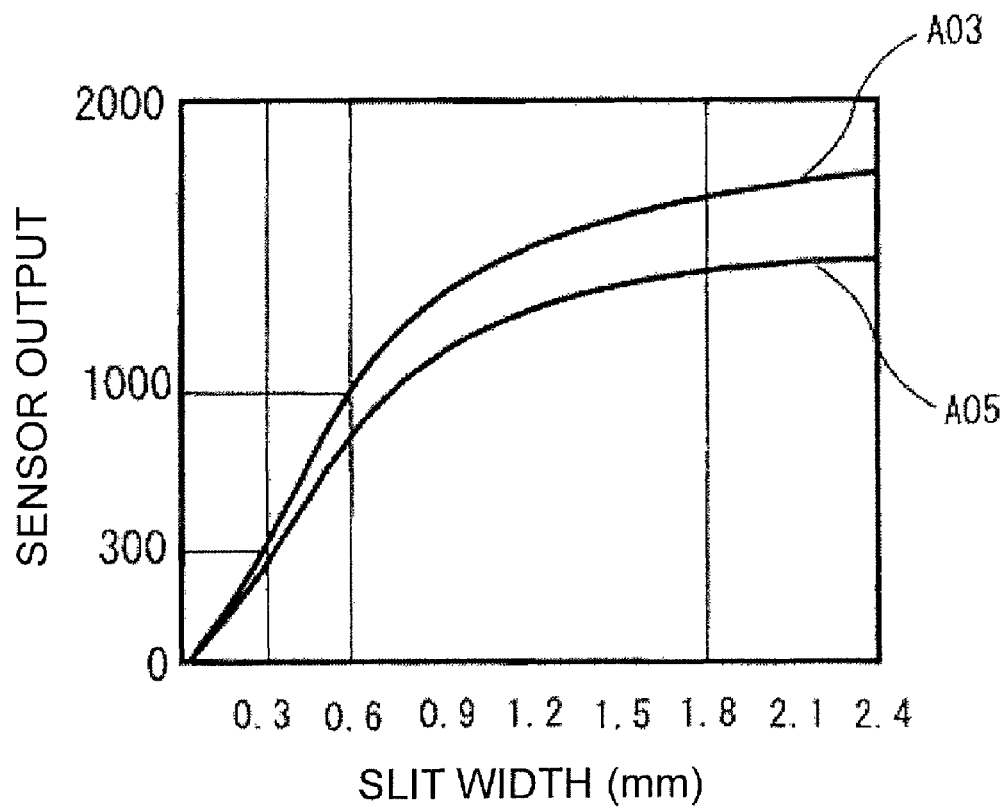
F I G. 8

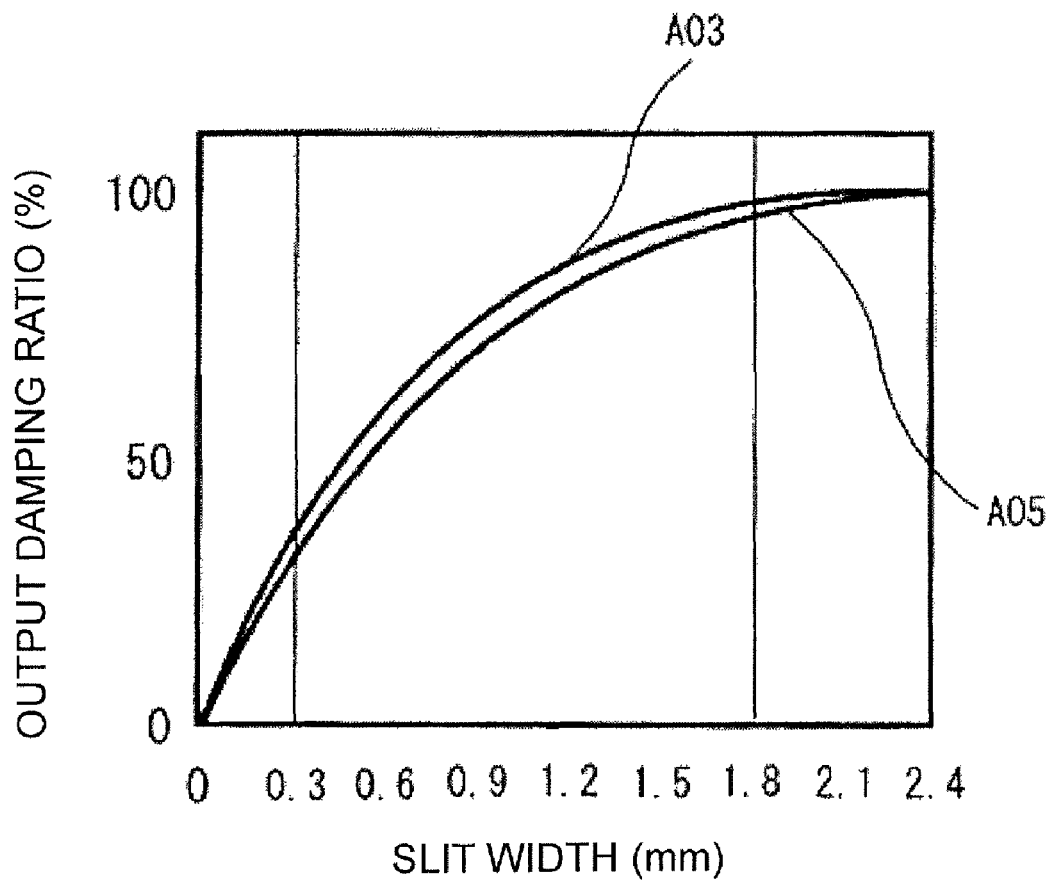
F I G. 9

X-RAY INSPECTION DEVICE

CROSS-REFERENCE TO RELATED APPLICATIONS

This application claims priority to Japanese Patent Application No. 2009-116105 filed on May 13, 2009, and Japanese Patent Application No. 2010-033442 filed on Feb. 18, 2010. The entire disclosures of Japanese Patent Application Nos. 2009-116105 and 2010-033442 are hereby incorporated herein by reference.

BACKGROUND

1. Technical Field

The present invention relates to an X-ray inspection device for irradiating articles with X-rays and detecting foreign matter in the articles.

2. Related Art

X-ray inspection devices or similar devices are conventionally used to detect foreign matter in articles. Research and development efforts are currently being conducted in relation to such devices.

In Japanese Laid-Open Patent Application Publication No. 2003-084066 (hereinafter "JP '066 publication"), there is disclosed a component of a radiation detector for minimizing the space required for wire bonding; making the radiation detector smaller in size and simpler to manufacture; and facilitating the manufacture of a two-dimensional detector. The component for a radiation detector is a component used in an X-ray inspection device.

The component of a radiation detector according to JP '066 publication includes a photoelectric element arranged on a portion of an upper surface of a substrate to output an electrical signal based on the intensity of light received by the photoelectric element. The photoelectric element has a first pad provided on its light-receiving surface. The component of a radiation detector has a pad-formation portion arranged on a portion of the substrate other than a portion where the photoelectric element is arranged, and a second pad formed on the pad formation section. The second pad is arranged to form the same plane as that of the first pad arranged on the light-receiving surface of the photoelectric element, and is electrically connected to the first pad.

Also, in JP '066 publication, there is also disclosed a component of a radiation detector that further includes an optical waveguide path provided upstream in the light-receiving direction of a light receiving surface of a photoelectric element (see claim 22 and FIG. 7 of JP '066 publication).

SUMMARY

For example, for the component of a radiation detector according to JP '066 publication, there is shown an example where a collimator is used as an optical waveguide path so that detection is performed using parallel light only (see FIG. 7 in JP '066 publication). However, in an instance where a photodiode array and a scintillator array are made to match in size and formed as a matrix as shown in FIG. 7 in JP '066 publication, the molding cost and other costs incurred during manufacture will be increased.

If a bonding step for bonding the scintillator array onto the photodiode array ("PDA" hereafter) using an optical adhesive is to be performed for reducing cost, the scintillator array must be made several millimeters wide, even if the width of the PDA is extremely small; i.e., about 0.1 to 0.9 mm.

In such a case, since the scintillator array is larger than the PDA, visible light converted by the scintillator array is diffracted with respect to the PDA, making it difficult to detect fine objects. This phenomenon will now be described with reference to FIG. 10.

FIG. 10 is a schematic cross-sectional view for describing a state in a conventional X-ray inspection device 900 that results in the detection of fine foreign matter being hindered.

As shown in FIG. 10, in a conventional X-ray inspection device 900, X-rays S1 are emitted from an X-ray emission device 200 and penetrate a conveyor belt 801, and visible light is emitted from scintillator elements 310a, 310b, 310c, 310d, and 310e of a scintillator 300. The visible light is received by a PDA 400, and an electrical signal is generated.

As described above, when X-rays S1 are emitted, the scintillator elements 310a, 310b, 310c, 310d, and 310e of the scintillator 300 emit visible light over 360 degrees in all directions. However, when fine foreign matter is present in an article that is conveyed by the conveyor belt 801, a scintillator element located below the fine foreign matter is not supposed to emit visible light. Nevertheless, due to the large number of scintillator elements, visible light converted by a scintillator element in the vicinity of a position below the fine foreign matter in the article will be received by the PDA 400. The edge of the fine foreign matter in the electrical signal generated by the PDA 400 thereby becomes less distinct, and detection of the fine foreign matter in the article becomes difficult.

An object of the present invention is to provide an X-ray inspection device capable of reliably detecting fine foreign matter using a simple mechanism.

An X-ray inspection device according to one aspect of the present invention is adapted to detect foreign matter in a target object while the target object is conveyed. The X-ray inspection device includes an X-ray emission device, a scintillator unit, a slit member and a photodiode array. The X-ray emission device is configured and arranged to emit X-rays at the target object. The scintillator unit is configured and arranged to optically convert the X-rays emitted by the X-ray emission device into visible light. The scintillator unit extends in a direction that intersects a conveyance direction of the target object. The slit member forms a slit that extends in the direction that intersects the conveyance direction. The slit member is disposed on an upstream side of the scintillator unit with respect to a direction of X-ray irradiation so that only the X-rays that passed through the slit enter the scintillator unit. The photodiode array is configured and arranged to detect the visible light optically converted by the scintillator unit and to convert the visible light into an electrical signal. The photodiode array is disposed along a direction in which the scintillator unit extends. The slit member is arranged so that a width of the slit is narrower than a width of the scintillator unit in the conveyance direction of the target object, and is equal to or wider than half a light-receiving width of the photodiode array in the conveyance direction of the target object.

BRIEF DESCRIPTION OF THE DRAWINGS

Referring now to the attached drawings which form a part of this original disclosure:

FIG. 3 is a schematic diagram showing a side view of the X-ray inspection device in FIG. 2;

FIG. 6 is a graph showing examples of MTF curves;

FIG. 8 is a graph showing examples of sensor output depending on slit width;

FIG. 9 is a graph showing examples of output damping ratio depending on slit width;

FIG. 11 is an enlarged schematic diagram showing a part of the conventional X-ray inspection device;

DETAILED DESCRIPTION OF EXEMPLARY EMBODIMENTS

An embodiment of the present invention will now be described with reference to the drawings.

Figure 2:
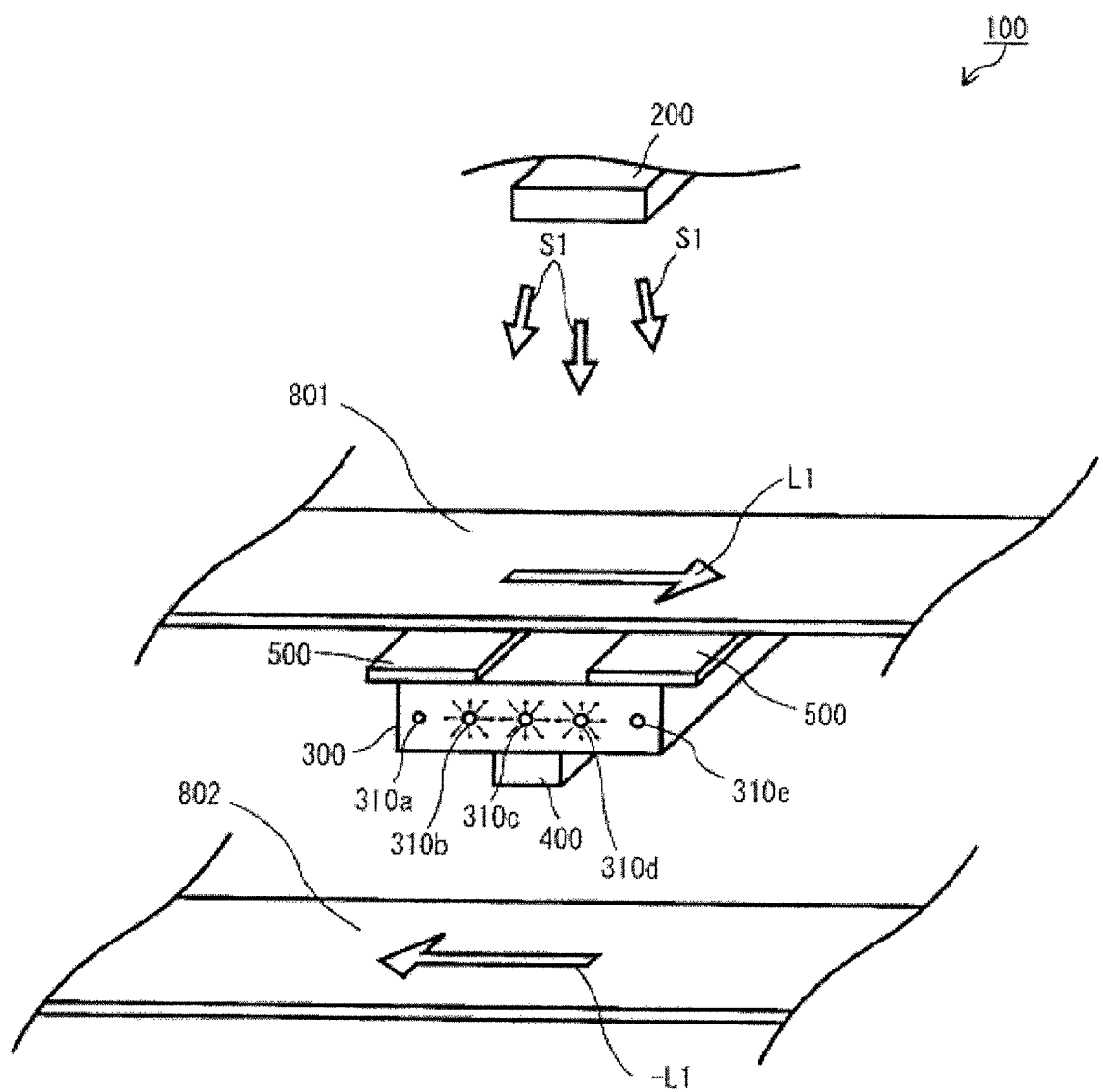
FIG. 2 is a schematic diagram showing an example of an interior of the X-ray inspection device according to the illustrated embodiment of the present invention.
Figure 1:
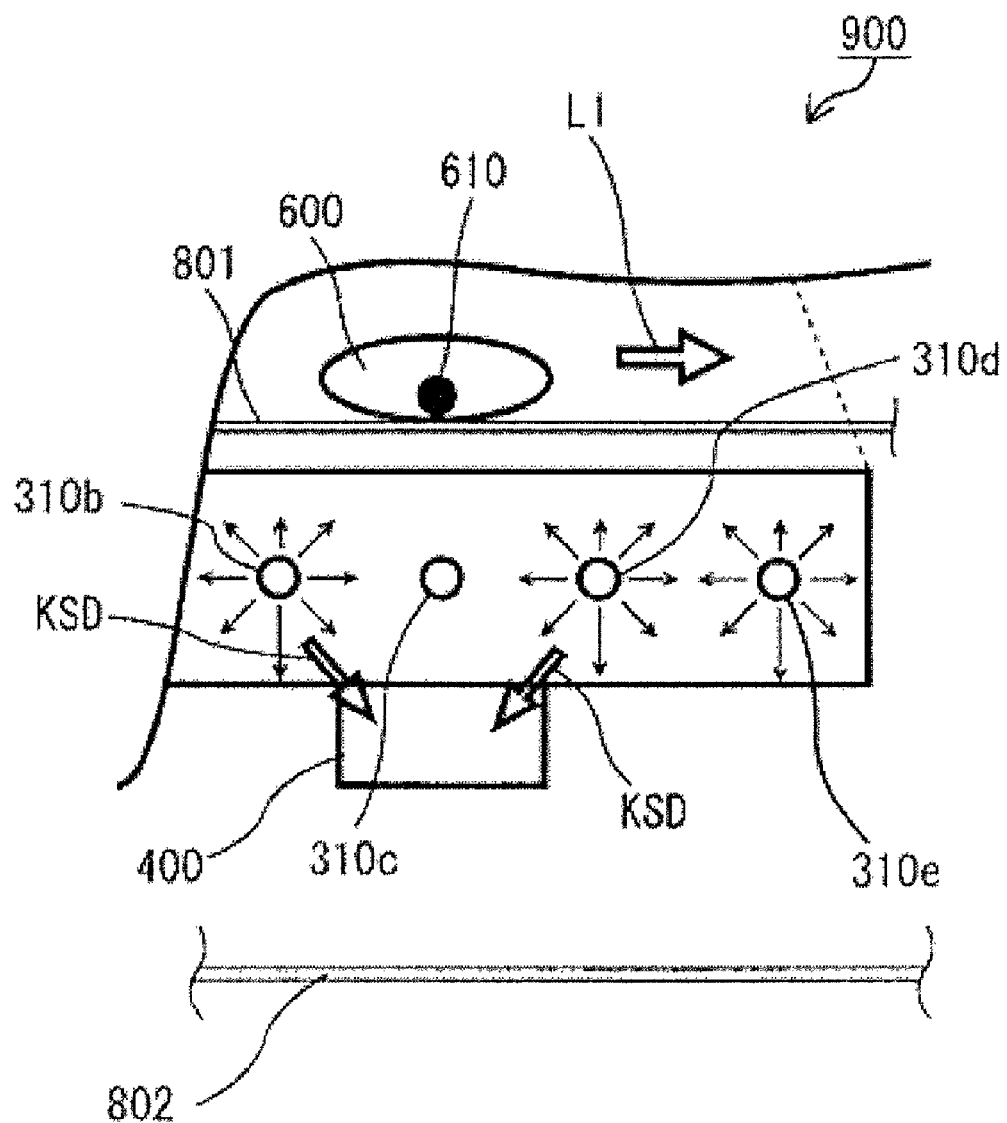
FIG. 1 is a schematic external view showing an example of an X-ray inspection device according to the illustrated embodiment of the present invention.

FIG. 1 is a schematic external view showing an X-ray inspection device 100 according to the present invention; and FIG. 2 is a schematic diagram showing an interior of the X-ray inspection device 100 according to the present invention.

As shown in FIG. 1, an X-ray emission device 200 is installed in the X-ray inspection device 100. A product to be examined is placed on a conveyor belt 800 and transported through the X-ray inspection device 100, during which time an X-ray inspection is performed therein to examine whether the products contain foreign matter.

As shown in FIG. 1, the conveyor belt 800 of the X-ray inspection device 100 is formed so as to protrude outwards from the X-ray inspection device 100, and a plurality of X-ray shielding curtains 850 are provided. An operator operates a touch panel MT to drive the X-ray inspection device 100. An internal structure of the X-ray inspection device 100 will now be described.

As shown in FIG. 2, the X-ray inspection device 100 according to the present invention includes the X-ray emission device 200, the conveyor belt 800, a slit member 500, an irradiation width adjustment mechanism 510 (see FIG. 3), a scintillator 300 (a scintillator unit), and a photodiode array ("PDA" hereafter) 400. The conveyor belt 800 includes an endless belt rolled around a pair of rollers. In FIG. 2, a portion of the belt travelling along a forward route is shown as a conveyor belt 801, and a portion of the belt travelling along a return route is shown as a conveyor belt 802. The slit member 500, the scintillator 300, and the PDA 400 are positioned in the stated sequence listed from the top; and are provided between the conveyor belt 801 and the conveyor belt 802, and the X-ray emission device 200 is provided above the conveyor belt 801. The conveyor belt 801 conveys an article in the conveyance direction indicated by the arrow L1. The conveyor belt 802 travels in the direction indicated by the arrow –L1, and thereby returns to the forward route side of the conveyor belt 801. In the present embodiment, damping of X-rays S1 is only affected by the conveyor belt 801 of the conveyor belts 801 and 802, and is not influenced by the conveyor belt 802.

X-rays S1 are emitted from the X-ray emission device 200 in FIG. 2. The conveyor belt 801, located above the slit member 500, the scintillator 300, and the PDA 400, conveys an article 600 in the conveyance direction indicated by the arrow L1.

As shown in FIG. 2, the scintillator 300 has scintillator elements $310a$, $310b$, $310c$, $310d$, and $310e$. For the purpose of description, there are five scintillator elements $310a$ through $310e$; however, in reality, the scintillator 300 has numerous scintillator elements. A slit formed by the slit member 500 in FIG. 2 extends in a direction perpendicular to the conveyance direction indicated by the arrow L1.

Figure 4:
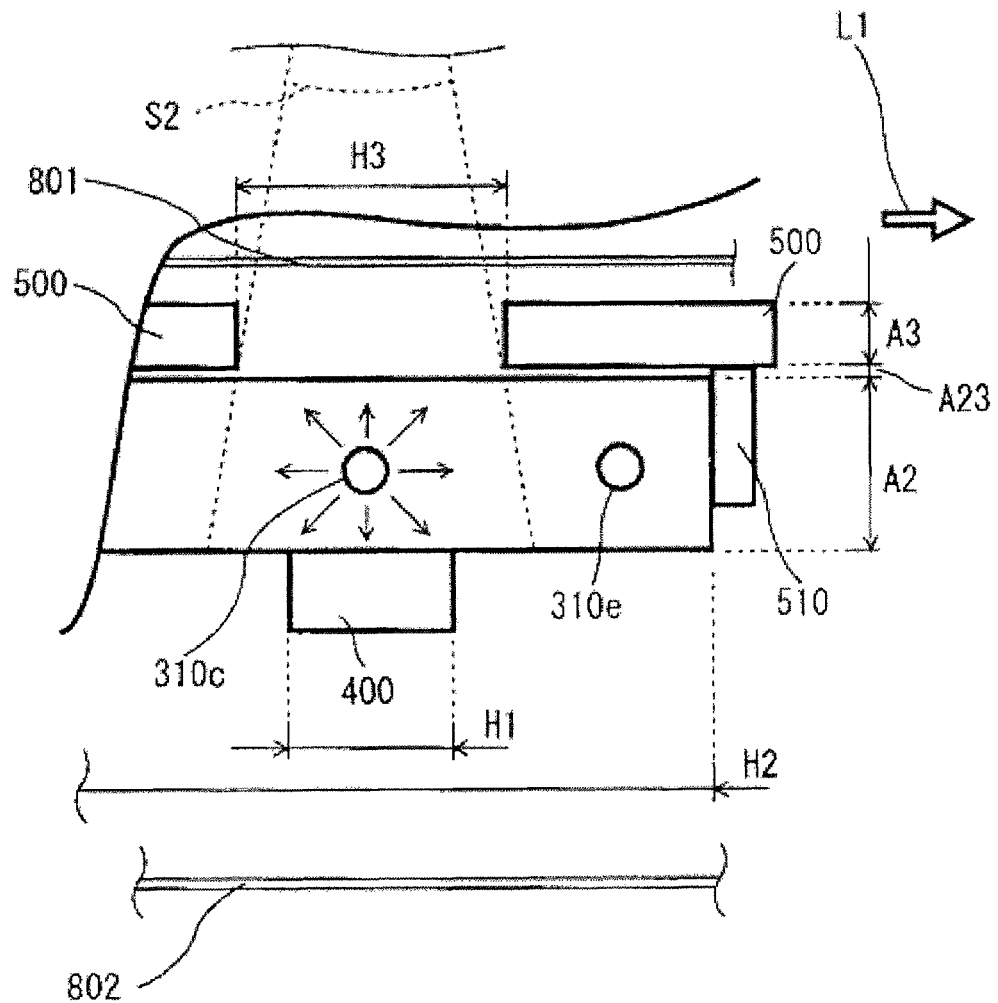
FIG. 4 is an enlarged schematic diagram showing a part of FIG. 3.
Figure 5:
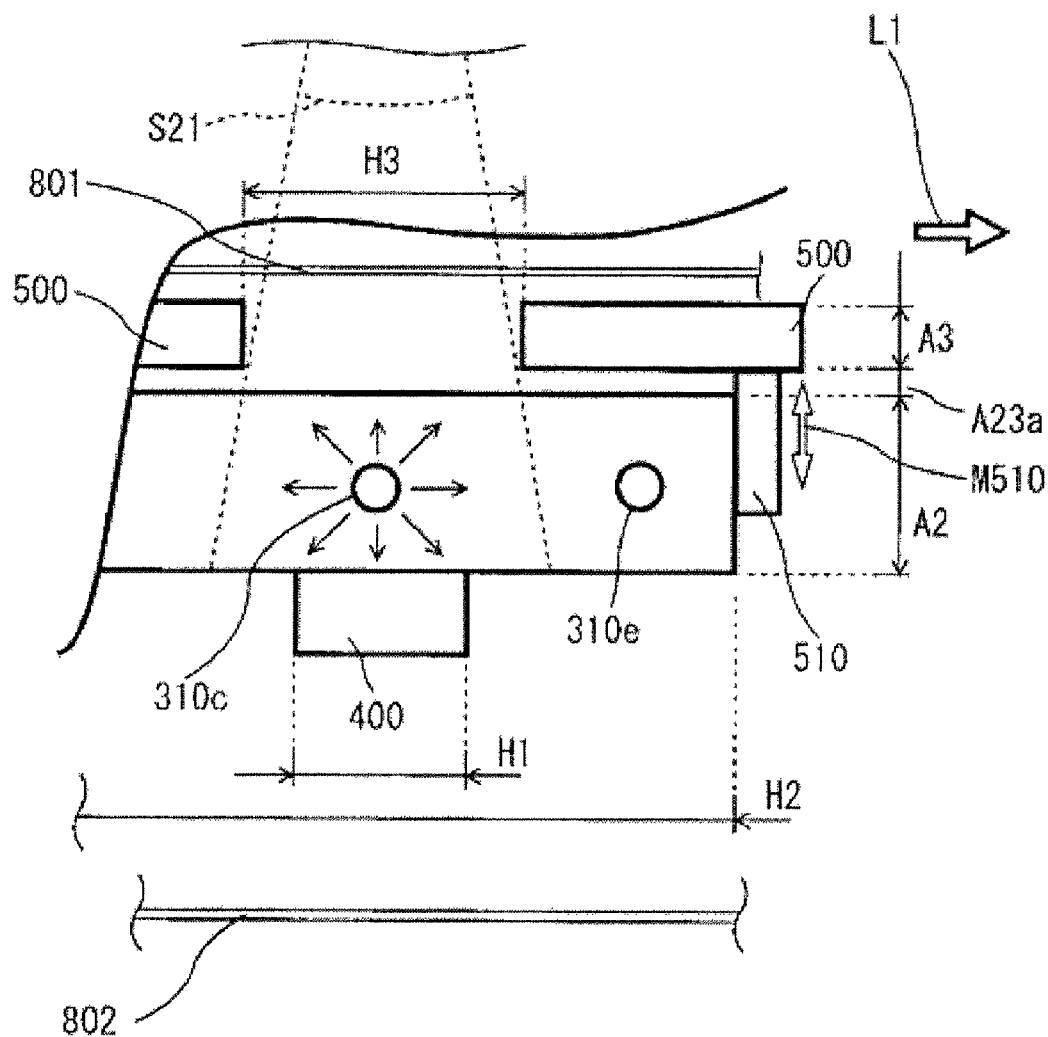
FIG. 5 is an enlarged schematic diagram showing a part of FIG. 3.

Next, the slit of the slit member 500 will be described with reference to FIGS. 3, 4, and 5. FIG. 3 is a schematic diagram showing a side view of the X-ray inspection device 100 in FIG. 2, and FIGS. 4 and 5 are enlarged schematic diagrams showing a part of FIG. 3. The scintillator element $310d$ is omitted in FIGS. 4 and 5.

As shown in FIG. 3, the scintillator 300 is affixed to the PDA 400 using a chemical adhesive. The X-ray emission device 200 emits the X-rays S1. In the present embodiment, the presence of the slit member 500 results in the scintillator 300 being irradiated only with X-rays within the range shown by X-rays S2, and the remaining X-rays S1 are reflected by the slit member 500. In other words, X-rays S2 are part of X-rays S1 within the range corresponding to the slit of the slit member 500. The slit and the X-rays S2 depend on the width at which the PDA 400 receives the visible light converted by the scintillator 300.

Figure 10:
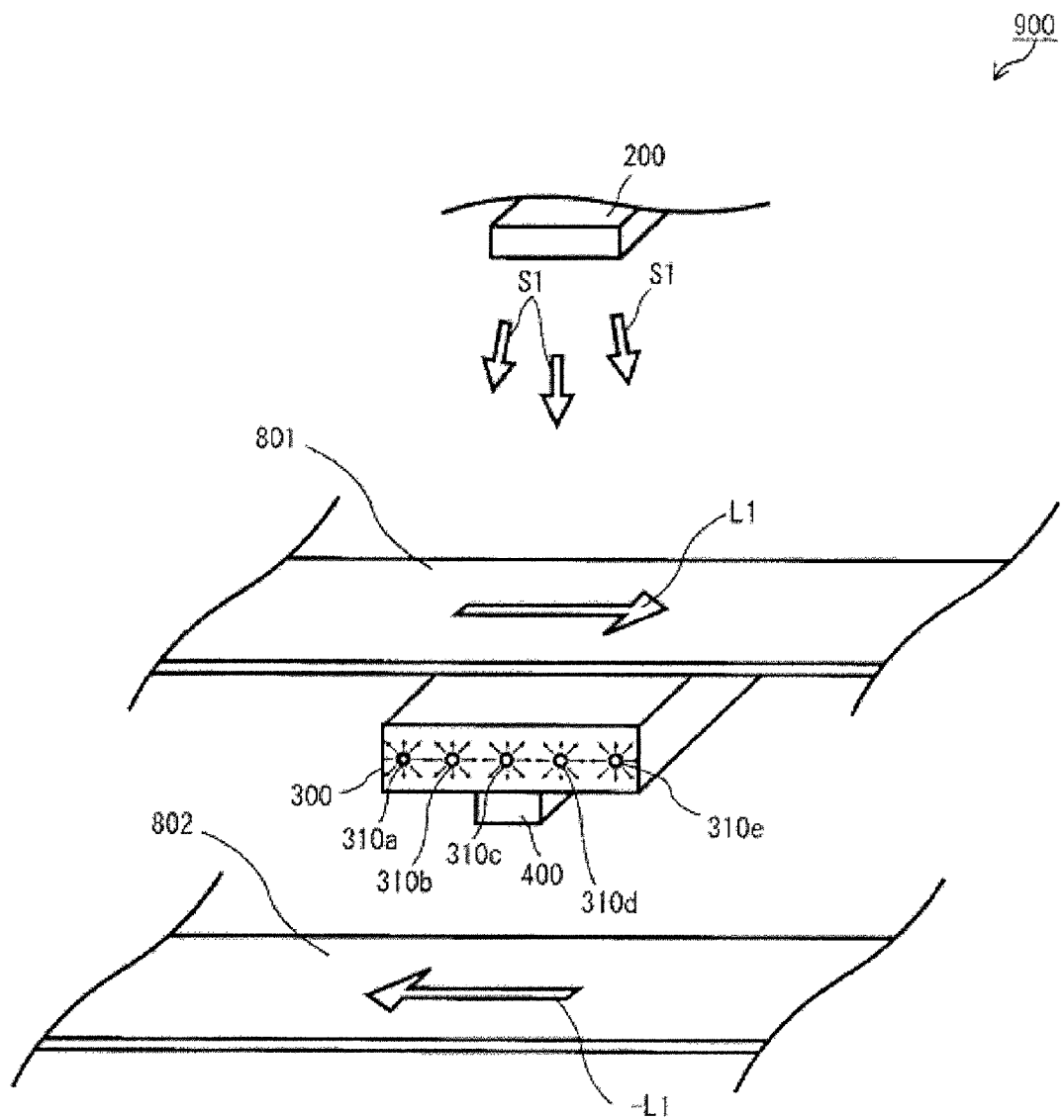
FIG. 10 is a schematic diagram for describing a conventional X-ray inspection device.

In the X-ray emission device 200 in a conventional X-ray inspection device 900 such as one shown in FIG. 10, the layer of the slit member 500 is not provided, and the scintillator 300 is therefore irradiated with X-rays within the range shown by X-rays S1. As a result, optical conversion into visible light also occurs even in the scintillator elements $310a$, $310e$ of the scintillator 300, and the PDA 400 receives the visible light from all of the scintillator elements $310a$ through $310e$. The outline of fine foreign matter in the article thereby becomes blurred even when fine foreign matter is present in the article, and detection of the fine foreign matter becomes difficult. A specific example of a state in which detection of fine foreign matter becomes difficult as described above will be given further below.

Next, as shown in FIG. 4, when H1 is the width of the PDA 400 as measured in the conveyance direction (L1), A2 and 112 are respectively the thickness of the scintillator 300 as measured in a vertical direction and the width of the scintillator 300 as measured in the conveyance direction (L1), A3 is the thickness of the slit member 500 as measured in the vertical direction, and H3 is the slit width as measured in the conveyance direction (L1), a relationship $H1 \leq H3 < H2$ exists.

Also, as shown in FIGS. 4 and 5, the irradiation width adjustment mechanism 510 is used to move the slit member 500 in the vertical direction (indicated by the arrow M510) to change the spacing between the scintillator 300 and the slit member 500 from a distance A23 to a distance A23a. The irradiation width of the X-rays S2 can thereby be changed to an irradiation width of X-rays S21. In such an instance, the irradiation width adjustment mechanism 510 can be used to adjust the width of irradiation of the X-rays S2 reaching the scintillator 300. For example, the vertical spacing between the scintillator 300 and the slit member 500 can be adjusted, whereby the irradiation width and the amount of X-rays S2 incident on the scintillator 300 can be adjusted.

Affixing the scintillator 300 to the PDA 400 using the chemical adhesive and providing the slit member 500, as described above, eliminates the need to manufacture the scintillator 300 so that the width H2 of the scintillator 300 matches the width H1 of the PDA 400. In other words, it is possible to ameliorate decreases in yield due to such problems as faulty adhesion between the scintillator 300 and the PDA 400 in cases where the scintillator 300 is manufactured to match the width H1 of the PDA 400. Also, it becomes possible to reduce the cost necessary to manufacture a small scintillator 300 that matches the width H1 of the PDA 400.

Also, it becomes possible to direct X-rays S2 or X-rays S21 only onto the minimum necessary portions of the scintillator 300, and to prevent X-rays from reaching unnecessary portions of the scintillator 300 (i.e., scintillator elements 310*a* and 310*e* in FIG. 3). It then becomes possible to prevent the PDA 400 from receiving an unintended large quantity of visible light due to optical conversion, and to prevent unnecessary visible light from reaching the PDA 400 due to diffraction of light.

Next, the relationship between the thickness A2 of the scintillator 300, the width H1 of the PDA 400, and the slit width H3, will be described with reference to FIGS. 6 through 9. An X-ray emission intensity of 50 kV was used in the following experiments. Also, the following experiments were performed under a condition in which the width H1 of the PDA 400 was 0.6 mm.

Figure 7:
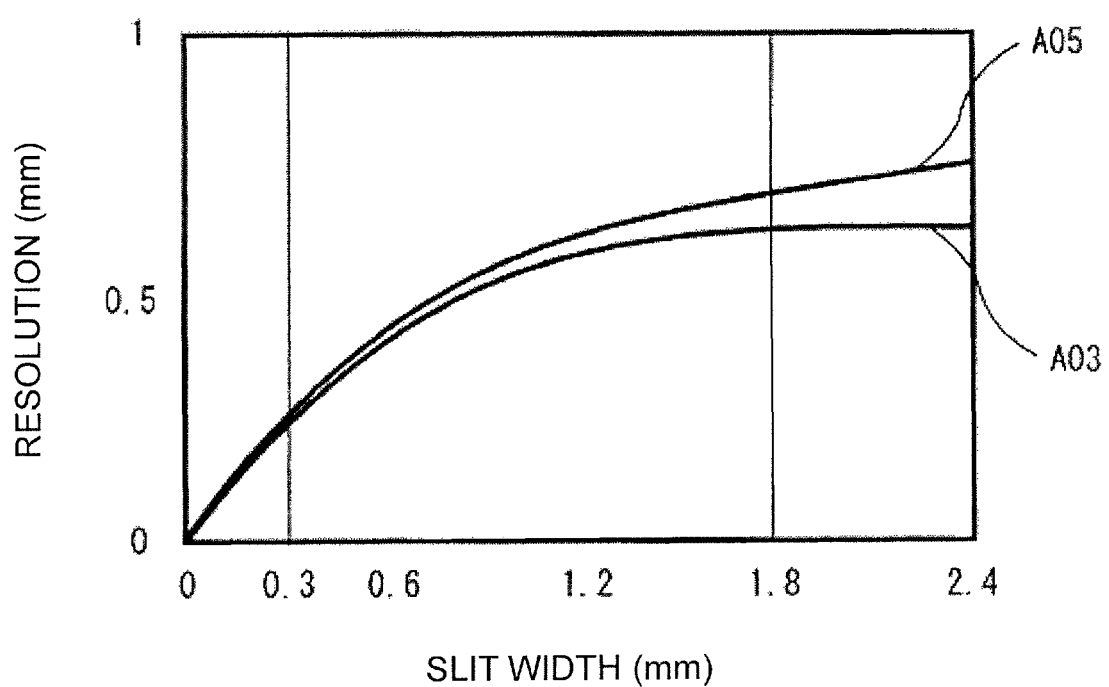
FIG. 7 is a graph showing examples of resolution depending on slit width.

FIG. 6 is a graph showing examples of MTF curves; FIG. 7 is a graph showing examples of resolution depending on slit width; FIG. 8 is a graph showing examples of sensor output depending on slit width; and FIG. 9 is a graph showing examples of output damping ratio depending on slit width.

Firstly, the MTF curves shown in FIG. 6 represent spatial frequency, which is the number of cycles per unit length (millimeter) in the horizontal axis, and the contrast reproduction capability (MTF: Modulation Transfer Function) normalized to 1 or 100 at zero frequency in the vertical axis. Here, the spatial frequency is a value that represents the spacing between each stripe in a regularly repeating black-and-white stripe pattern.

The experiment relating to FIG. 6 was performed under a condition in which the thickness A2 of the scintillator 300 was 0.3 mm. A plurality of types of slit members 500, having widths H3 measuring 0.6 mm, 0.9 mm, 1.2 mm, 1.5 mm, and 1.8 mm respectively, were prepared, and the experiment was performed in the presence of each type of slit member 500, as well as in the absence of slit member 500.

In FIG. 6, curve T06 represents an instance where the slit width H3 was 0.6 mm; curve T09 represents an instance where the slit width H3 was 0.9 mm; curve T12 represents an instance where the slit width H3 was 1.2 mm; curve T15 represents an instance where the slit width H3 was 1.5 mm; curve T18 represents an instance where the slit width H3 was 1.8 mm; and curve T0 represents an instance where no slit member 500 was provided.

From the results shown in FIG. 6, it can be seen that a higher spatial frequency can be maintained in curve T06, curve T09, curve T12, curve T15, curve T18, and curve T0 in the stated order.

In other words, a higher spatial frequency can be maintained when there is a slit member forming a slit as compared to when there is no slit member. And thus, it is preferable to provide a slit member to the X-ray inspection device.

Next, the horizontal axis in FIG. 7 represents slit width H3 (mm), and the vertical axis represents resolution (mm). In FIG. 7, the inverse of the value of the spatial frequency at the point where the MTF value first falls below 0.1 was defined as the resolution (mm).

In FIG. 7, curve A03 represents an instance where the thickness A2 of the scintillator 300 is 0.3 mm, and curve A05 represents an instance where the thickness A2 of the scintillator 300 is 0.5 mm. Each of curves A03 and A05 is a polynomial approximation curve, estimated from points corresponding to the slit width H3 being changed to 0.6 mm, 0.9 mm, 1.2 mm, 1.5 mm, 1.8 mm, and 2.4 mm, respectively.

As shown in FIG. 7, the curve A03 has a higher resolution in all regions compared to the curve A05; as a result, it can be seen that the resolution is higher in the present experiment when the thickness A2 of the scintillator 300 is 0.3 mm than when the thickness A2 is 0.5 mm.

Also, the results shown in FIG. 7 show that the resolution becomes constant on the curve A03 at a slit width H3 of over 1.8 mm. As a result, the upper limit of the slit width H3 is 1.8 mm; increasing the slit width H3 to over 1.8 mm offers no benefit.

Next, in FIG. 8, the horizontal axis represents slit width (mm), and the vertical axis represents sensor output. Here, the sensor output represents the value of the electrical signal output from the PDA 400.

In FIG. 8, curve A03 represents an instance where the thickness A2 of the scintillator 300 is 0.3 mm, and curve A05 represents an instance where the thickness A2 of the scintillator 300 is 0.5 mm. Each of curves A03 and A05 is a polynomial approximation curve, estimated from points corresponding to the slit width H3 being changed to 0.6 mm, 0.9 mm, 1.2 mm, 1.5 mm, 1.8 mm, and 2.4 mm, respectively.

As shown in FIG. 8, the curve A03 has a higher sensor output value than the curve A05, showing that optical conversion is more efficient when the thickness A2 of the scintillator 300 is 0.3 mm than when the thickness A2 is 0.5 mm.

Also, FIG. 8 shows that the sensor output becomes constant at a slit width H3 of over 1.8 mm. As a result, the upper limit of the slit width H3 is 1.8 mm; increasing the slit width H3 to over 1.8 mm offers no benefit. Also, since images can be processed when the lower limit of the sensor output is approximately 300 or above, the lower limit of the slit width H3 is 0.3 mm.

When the signal-to-noise ratio in the sensor output is taken into consideration, it is preferable for the noise to have a constant value and the signal to be larger. In order to perform image processing more properly, it is preferable for the sensor output to be about 1000 or higher. Therefore, when the thickness A2 of the scintillator 300 is 0.3 mm, the lower limit of the slit width H3 is preferably approximately 0.6 mm.

As described above, the slit width H3 is preferably between 0.3 mm and 1.8 mm. In an instance where the thickness A2 of the scintillator 300 is 0.3 mm, the upper limit of the slit width H3 is 1.8 mm, and the ratio between the thickness A2 of the scintillator 300 and the upper limit of the slit width H3 is therefore 1:6. In an instance where the thickness A2 of the scintillator 300 is 0.3 mm, the lower limit of the slit width H3 is 0.3 mm, and the ratio between the thickness A2 of the scintillator 300 and the lower limit of the slit width H3 is therefore 1:1.

Therefore, the ratio between the thickness A2 of the scintillator 300 and the slit width H3 is preferably between 1:6 and 1:1. In such an instance, the X-rays that had passed through the slit can be optically converted in the scintillator 300 with a high degree of efficiency.

As described above, in an instance where the width H1 of the PDA 400 is 0.6 mm, the upper limit of the slit width H3 is 1.8 mm, and the ratio between the width H1 of the PDA 400 and the upper limit of the slit width H3 is therefore 1:3. Also, in an instance where the width H1 of the PDA 400 is 0.6 mm, the lower limit value of the sensor output is approximately 300 and the lower limit of the slit width H3 is 0.3 mm, and the ratio between the width H1 of the PDA 400 and the lower limit of the slit width H3 is therefore 2:1.

Also, as described above, in order to perform image processing more properly, the sensor output is preferably about 1000 or higher; therefore, the lower limit of the slit width H3 is 0.6 mm. Also, since the width H1 of the PDA 400 is 0.6 mm, the ratio between the width H1 of the PDA 400 and the lower limit of the slit width H3 is 1:1.

Accordingly, the ratio between the width H1 of the PDA 400 and the slit width H3 is preferably between 2:1 and 1:3, and more preferably between 1:1 and 1:3. Thus, the slit width H3 is narrower than the scintillator unit width H2 and equal to or wider than half a width of the light-receiving width H1 of the photodiode array 400. Therefore, a high level of resolution and electrical signal in the photodiode array 400 can be maintained.

Finally, in FIG. 9, the horizontal axis represents slit width (mm), and the vertical axis represents the output damping ratio (%).

In FIG. 9, the curve A03 represents an instance where the thickness A2 of the scintillator 300 is 0.3 mm, and the curve A05 represents an instance where the thickness A2 of the scintillator 300 is 0.5 mm. Each of curves A03 and A05 is a polynomial approximation curve, estimated from points corresponding to the slit width H3 being changed to 0.6 mm, 0.9 mm, 1.2 mm, 1.5 mm, 1.8 mm, and 2.4 mm, respectively.

As shown in FIG. 9, the curve A03 displays a greater output damping ratio than the curve A05, and a higher output damping ratio (%) is maintained in an instance where the thickness A2 of the scintillator 300 is 0.3 mm in comparison to when the thickness A2 is 0.5 mm.

As shown by FIGS. 6 though 9 described above, it can be seen that in an instance where the width H1 of the PDA 400 is 0.6 mm, the thickness A2 of the scintillator 300 is preferably 0.3 mm, and the slit width H3 of the slit formed by the slit member 500 is preferably within the range of between 0.6 mm and 1.8 mm.

Next, differences between the conventional X-ray inspection device 900 and the X-ray inspection device 100 according to the present invention will be described with reference to FIGS. 10 through 14. FIGS. 10 and 11 are schematic views for describing the conventional X-ray inspection device 900, and FIGS. 12 and 13 are schematic views for describing the X-ray inspection device 100 according to the present invention.

In the conventional X-ray inspection device 900 shown in FIGS. 10 and 11, X-rays S1 are emitted by the X-ray emission device 200, and the article 600 having fine foreign matter 610 is conveyed in the conveyance direction indicated by the arrow L1. In such an instance, the X-rays S1 hardly penetrate the fine foreign matter 610 in the article 600. Therefore, the X-rays S1 are hardly incident on the scintillator element 310c of the scintillator 300, and it is only the scintillator element 310c where the X-rays are hardly converted into visible light.

However, the scintillator elements 310a, 310b, 310d, and 310e emit visible light in all directions; therefore, visible light KSD (i.e., diffracted light) travelling in a diagonal direction reaches the PDA 400 as shown in FIG. 11. Accordingly, in an instance where the fine foreign matter 610 in the article 600 is extremely small, there may be an instance where no difference appears in the electrical output signal outputted by the PDA 400, and the presence of the fine foreign matter 610 in the article 600 is not identified. In other words, the visible light KSD substantially cancels out a variation caused by the fine foreign matter 610. Here, the visible light KSD is an integrated light of visible light emitted by the scintillator elements 310a and 310b and travelling in a downward direction at about 45 degrees angle, and visible light emitted by the scintillator elements 310d and 310e and travelling in a downward direction at about 45 degrees angle.

Figure 12:
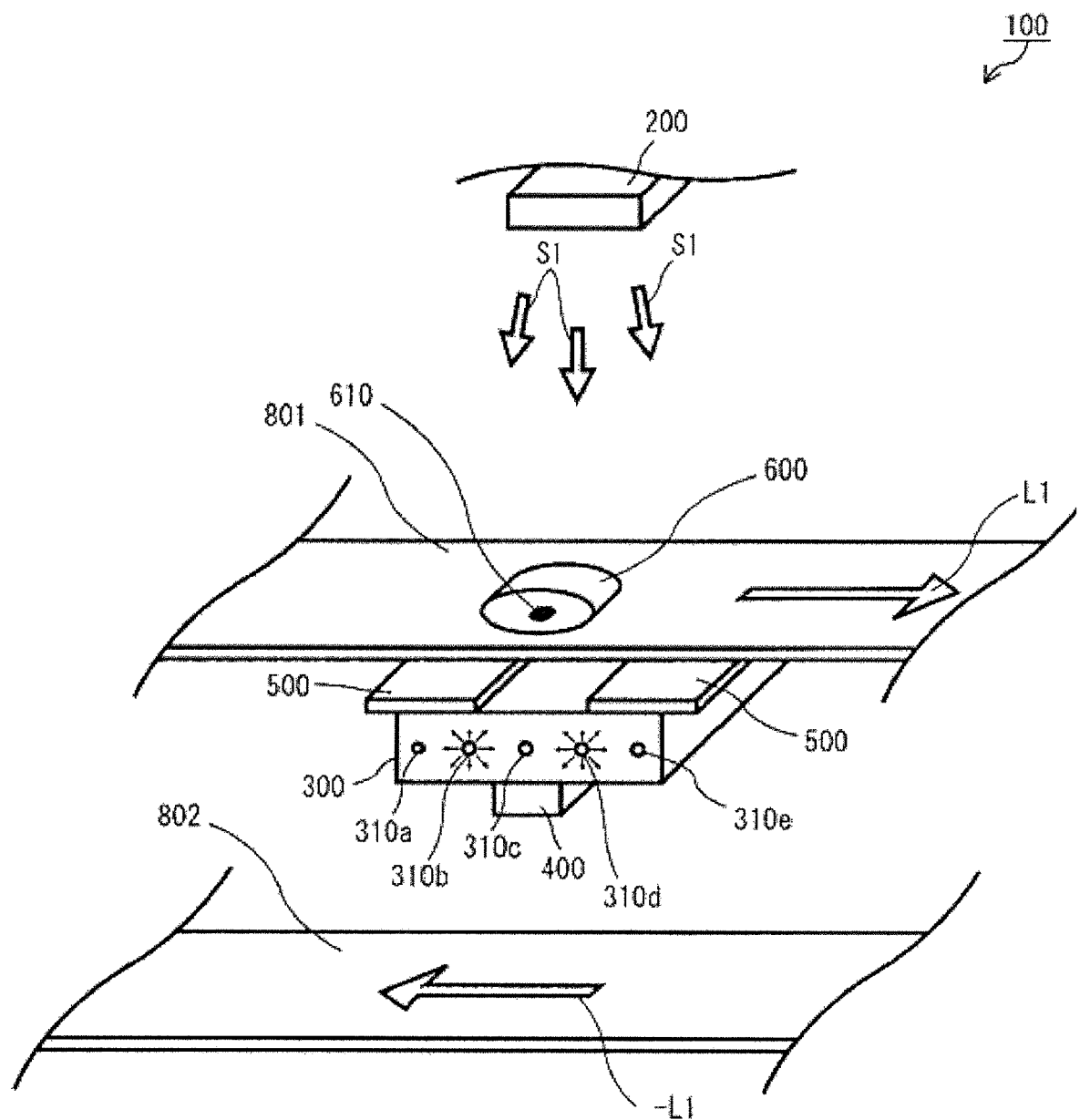
FIG. 12 is a schematic diagram for describing the X-ray inspection device according to the illustrated embodiment of the present invention.
Figure 13:
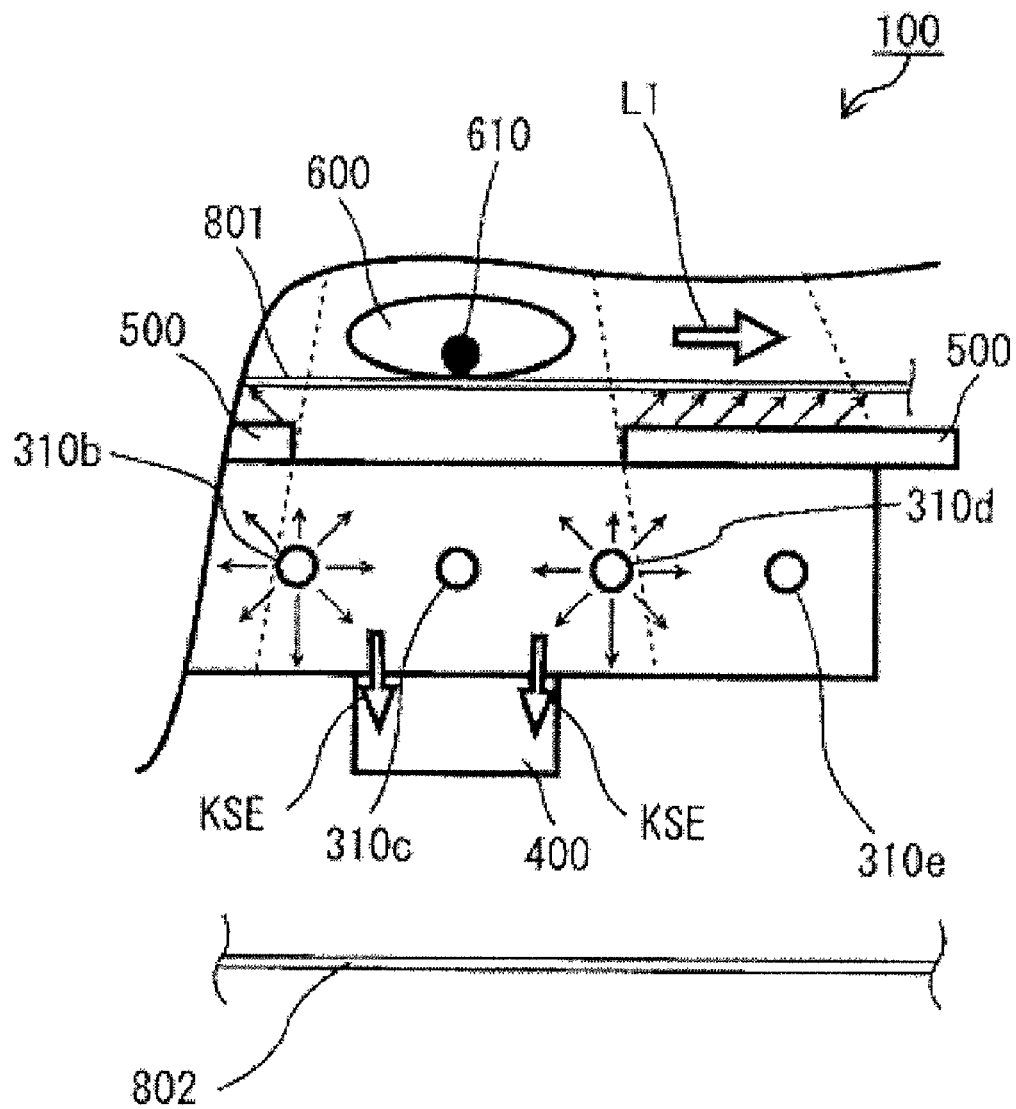
FIG. 13 is a schematic diagram for describing the X-ray inspection device according to the illustrated embodiment of the present invention.

In contrast, in the X-ray inspection device 100 according to the present invention shown in FIGS. 12 and 13, the X-rays S1 are emitted by the X-ray emission device 200; however, the presence of the slit member 500 causes the scintillator 300 to be irradiated with X-rays S2 having a narrower width than the X-rays S1. The article 600 is then conveyed in the conveyance direction indicated by the arrow L1.

In such an instance, the fine foreign matter 610 in the article 600 and the slit member 500 hardly allow the X-rays S1 to penetrate therethrough. Therefore, the scintillator elements 310a, 310c, and 310e of the scintillator 300 are hardly irradiated with the X-rays S1 and X-rays S2. As a result, the effect of diffracted visible light from the sides of scintillator elements 310a and 310e towards the side of the scintillator element 310c can be significantly reduced.

As a result, the PDA 400 is hardly exposed to the diagonally travelling visible light KSD as shown in FIG. 11, and is exposed to visible light KSE travelling downwards in a substantially vertical direction as shown in FIG. 13. In other words, the scintillator elements 310a and 310e hardly perform optical conversion; the visible light KSE is an integrated light of visible light travelling almost directly downwards and visible light travelling in a downward direction at about 45 degrees angle emitted by the scintillator element 310b, and visible light travelling almost directly downwards and visible light travelling in a downward direction at about 45 degrees angle emitted by the scintillator element 310d. As a result, even in an instance where the fine foreign matter 610 in the article 600 is extremely small, a difference appears in visible light reaching the PDA 400, making it possible to reliably detect the fine foreign matter 610 in the article 600.

Figure 14:
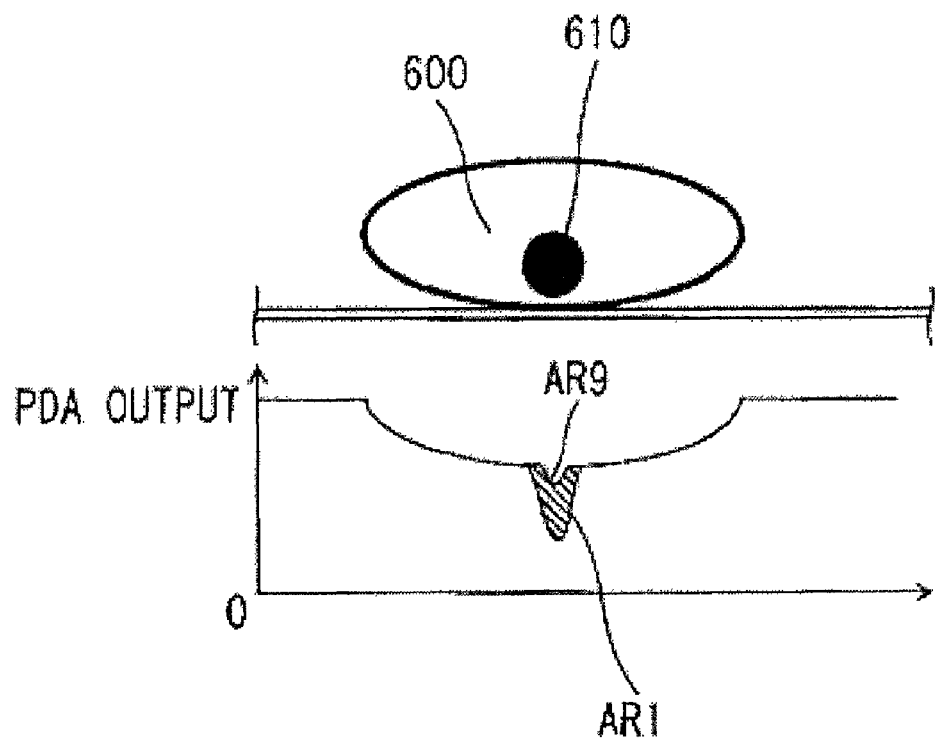
FIG. 14 is a drawing for describing an effect of the illustrated embodiment of the present invention.

An effect of the present invention will now be described with reference to FIG. 14. FIG. 14 is a drawing for describing an effect of the present invention. The vertical axis represents the electrical signal outputted by the PDA 400, and the horizontal axis represents time.

As shown in FIG. 14, in an instance where a conventional X-ray inspection device 900 is used, diffraction occurs, and visible light KSD is generated; therefore, the fine foreign matter 610 of the article 600 only appears in region AR9.

In contrast, in an instance where the X-ray inspection device 100 according to the present invention is used, light can be prevented from diffracting, and the visible light KSE causes the fine foreign matter 610 in the article 600 to be visible within region AR1. As described above, the region AR1 is several times greater than the region AR9; therefore, the fine foreign matter 610 can be reliably detected.

As described above, in the X-ray inspection device 100 according to the present invention, the presence of the slit member 500 causes the X-rays S1 to reach only the minimum necessary area of the scintillator 300 for the PDA 400 ultimately to receive the visible light. As a result, in an instance where fine foreign matter is being detected, the presence of the slit member 500 prevents the X-rays S1 from reaching the portion of the scintillator 300 located in the vicinity below the fine foreign matter, and therefore diffracting of the visible light can be prevented.

Furthermore, the width H3 of the slit defined by the slit member 500 is smaller than the width H2 of the scintillator 300, and larger than the width H1 of the photodiode array 400. As a result, the X-rays S2 that had passed through the slit of the slit member 500 can be reliably optically converted by the scintillator 300 and converted to an electrical signal by the photodiode array 400.

Furthermore, since there is no need to manufacture the scintillator 300 so as to match the width H1 of the photodiode array 400, the cost of manufacturing the X-ray inspection device 100 can be reduced.

Furthermore, since the slit of the slit member 500 is provided in a direction that intersects the conveyance direction of the article indicated by the arrow L1, a shadow of the fine foreign matter 610 in the article 600 that passes above the slit member 500 can be made sharper. As a result, it is possible to reliably detect the fine foreign matter 610 in the article 600 using a simple mechanism.

Furthermore, since there is no obstacle between the X-ray emission device 200 and the article 600, the X-rays reach the scintillator 300 through the slit member 500 without loss of intensity. As a result, it is possible to adjust the intensity of the X-rays as appropriate and perform X-ray inspection in an efficient manner.

In the present embodiment, the article 600 corresponds to a target object, the X-rays S1, S2 correspond to X-rays, the X-ray emission device 200 corresponds to an X-ray emission device, the scintillator 300 corresponds to a scintillator, the photodiode array 400 corresponds to a photodiode array, the slit member 500 corresponds to a slit member, the slit width H3 corresponds to the width of the slit, the width H2 of the scintillator 300 corresponds to the width of the scintillator, the width H1 of the photodiode array 400 corresponds to the light-receiving width of the photodiode array, the arrow L1 corresponds to the conveyance direction, the irradiation width adjustment mechanism 510 corresponds to an irradiation width adjustment mechanism, and the X-ray inspection device 100 corresponds to an X-ray inspection device.

Accordingly, with the X-ray inspection device according to the illustrated embodiment, the X-ray emission device emits X-rays at the target object, the X-rays pass through the slit of the slit member, the scintillator unit optically converts the X-rays into visible light, and the photodiode array detects the optically converted visible light and converts the visible light into an electrical signal.

In such an instance, the width of the slit of the slit member is narrower than that of the scintillator unit, and is equal to or wider than half the light-receiving width of the photodiode array. As a result, X-rays that have passed through the slit of the slit member can be reliably optically converted by the scintillator unit and converted to an electrical signal by the photodiode array. Also, in an instance where fine foreign matter in the target object is being detected, the slit member can prevent visible light from being diffracted and make the edge of the fine foreign matter sharper. Fine foreign matter can thereby be reliably detected using a simple mechanism.

According to the illustrated embodiment, the slit member can prevent visible light from being diffracted and increase the sharpness of the edge of fine foreign matter in a target object. Fine foreign matter can thereby be reliably detected using a simple mechanism.

A preferred embodiment of the present invention was described above, but is not provided by way of limitation to the present invention. It should be appreciated that a variety of other embodiments are possible without departing from the spirit or the scope of the present invention. Furthermore, actions and advantageous effects of a configuration according to the present invention were described in the present embodiment; however, these actions and advantageous effects are merely cited by way of example, and are not provided by way of limitation to the present invention.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An X-ray inspection device adapted to detect foreign matter in a target object while the target object is conveyed, the X-ray inspection device comprising:
    an X-ray emission device configured and arranged to emit X-rays at the target object;
    a scintillator unit configured and arranged to optically convert the X-rays emitted by the X-ray emission device into visible light, the scintillator unit extending in a direction that intersects a conveyance direction of the target object;
    a slit member forming a slit that extends in the direction that intersects the conveyance direction, the slit member disposed on an upstream side of the scintillator unit with respect to a direction of X-ray irradiation so that only the X-rays that passed through the slit enter the scintillator unit; and
    a photodiode array configured and arranged to detect the visible light optically converted by the scintillator unit and to convert the visible light into an electrical signal, the photodiode array being disposed along a direction in which the scintillator unit extends,
    the slit member being arranged so that a width of the slit is narrower than a width of the scintillator unit in the conveyance direction of the target object, and is equal to or wider than half a light-receiving width of the photodiode array in the conveyance direction of the target object.

2. The X-ray inspection device according to claim 1, further comprising
    an irradiation width adjustment mechanism configured and arranged to adjust a width of irradiation of the X-rays reaching the scintillator unit through the slit.

3. The X-ray inspection device according to claim 1, wherein
    a ratio between the light-receiving width of the photodiode array and the width of the slit is within a range of 1:1 and 1:3.

4. The X-ray inspection device according to any of claim 1, wherein
a ratio between a thickness of the scintillator unit and the width of the slit is within a range of 1:1 and 1:6.

5. The X-ray inspection device according to claim 2, wherein
a ratio between the light-receiving width of the photodiode array and the width of the slit is within a range of 1:1 and 1:3.

6. The X-ray inspection device according to any of claim 5, wherein
a ratio between a thickness of the scintillator unit and the width of the slit is within a range of 1:1 and 1:6.

* * * * *